US006047109A

United States Patent [19]
Whittaker

[11] Patent Number: 6,047,109
[45] Date of Patent: Apr. 4, 2000

[54] METHODS AND SYSTEMS FOR RE-EVALUATING ASSEMBLY CONSENSUS SEQUENCES

[75] Inventor: Alex J. Whittaker, London, United Kingdom

[73] Assignee: SmithKline Beecham p.l.c., Brentford Middlesex, United Kingdom

[21] Appl. No.: 09/126,006

[22] Filed: Jul. 29, 1998

[51] Int. Cl.[7] ..................................................... G06F 15/18
[52] U.S. Cl. ................................ 395/13; 435/6; 435/91.1; 435/91.2; 702/27; 702/30; 702/22
[58] Field of Search ............................ 435/6, 91.1, 91.2; 395/13; 702/27, 30, 22

[56] References Cited

PUBLICATIONS

Gotoh, Osamu. "Optical Alignment Between Groups . . ." Cabios vol. 9, No. 3. 1993. pp. 361–370, Nov. 1998.
Birney et al., "PairWise and SearchWise: Finding the Optimal Alignment in a Simultaneous Comparison of a Protein Profile Against all DNA Translation Frames", *Nucleic Acids Research*, vol. 24(14), pp. 2730–2739 (1996).
Boguski et al., dbEST—Database for "Expressed Sequence Tags", *Nature Genetics*, vol. 4, pp. 332–333 (1993).
Bonfield et al., A New DNA Sequence Assembly Program, *Nucleic Acids Research*, vol. 23(24), pp. 4992–4999 (1995).
Brown et al., "Frame: Detection of Genomic Sequencing Errors", *Bioinformatics*, vol. 14(4), pp. 367–371 (1998).
J. Fickett, "Recognition of Protein Coding Regions in DNA Sequences", *Nucleic Acid Research*, vol. 10(17), pp. 5303–5318 (1982).
W. Gish and D. States, "Identification of Protein Coding Regions by Database Similarity Search", *Nature Genetics*, vol. 3, pp. 266–272 (1993).
X. Huang, "A Contig Assembly Program Based on Sensitive Detection of Fragment Overlaps", *Genomics*, vol. 14(1), pp. 18–25 (1992).
Petola et al., "SEQAID: A DNA Sequence Assembling Program Based on a Mathematical Model", *Nucleic Acids Research*, vol. 12(1), pp. 307–321 (1984).
J. Posfai and R. Roberts, "Finding Errors in DNA Sequences", Proc. Natl. Acad. Sci. USA, vol. 89, pp. 4698–4702, (1992).
M. Saqi, "An Analysis of Structural Instances of Low Complexity Sequence Segments", *Protein Engineering*, vol. 8(11), pp. 1069–1073 (1995).
R. Staden, "Automation of the Computer Handling of Gel Reading Data Produced by the Shotgun Method of DNA Sequencing", *Nucleic Acids Research*, vol. 10(15), (1982).
I. Ladunga and R. Smith, "Amino Acid Substitutions Preserve Protein Folding by Conserving Steric and Hydrophobicity Properties", *Protein Engineering*, vol. 10(3), pp. 187–196 (1997).
Solovyev et al., "Predicting Internal Exons by Oligonucleotide Composition and Discriminant Analysis of Spliceable Open Reading Frames", *Nucleic Acids Research*, vol. 22(24), pp. 5156–5163 (1994).

*Primary Examiner*—Eggerton A. Campbell
*Assistant Examiner*—Janell E. Taylor
*Attorney, Agent, or Firm*—James M. Kanagy; Charles M. Kinzig; Keith Rutter

[57] ABSTRACT

A computational method maximizing open reading frame length in an assembly consensus sequence is provided. Systems employing the method are also provided.

7 Claims, 3 Drawing Sheets

METHODS AND SYSTEMS FOR RE-EVALUATING ASSEMBLY CONSENSUS SEQUENCES

FIELD OF THE INVENTION

This invention relates to computer-based methods and systems for assembly of consensus sequences from EST data.

BACKGROUND OF THE INVENTION

Expressed Sequence Tags (ESTs) are sequenced from mRNA in a known direction, from a random start point, for a length of approximately 100 to 400 bases. The sequencing reliability is variable across the length of the EST but generally in excess of 95% accuracy. The cDNA encoding an EST comes from a single clone and there are often several ESTs generated. The goal of the assembly process is to collect all ESTs derived from the clones encoding a particular gene and combine them into a multiple sequence alignment. A consensus of that sequence is generated and this is taken to be the cDNA sequence of the underlying gene which allows further analysis on its relationship to known proteins, many of which only become apparent at the amino acid level. The sequence errors inherent in the EST generation process, namely miscalls, unknowns, insertions and deletions lead to inconsistencies in the multiple sequence alignment. It is possible for these errors to be propagated into the assembly consensus where they occur in several ESTs or there is low coverage, i.e., few ESTs align over the corresponding part of the multiple sequence alignment. Miscalls and unknowns may lead to the insertion of a stop codon in the correct reading frame. Insertions and deletions will lead to a frameshift. These events make the prediction of the correct open reading frame very difficult. Inconsistencies in a multiple sequence alignment are generally resolved by a majority vote. Where there is disagreement between EST components of an assembly about what base to enter at a particular site, the base that occurs most frequently at that point in all the ESTs is chosen. Where there is no clear majority some heuristic must be applied to determine the "best" consensus. In many cases, this heuristic is largely frequentistic, order-dependent or ad hoc and ignores the fact that the consensus cDNA sequence should code for a protein sequence. Since the aim of EST assembly is to improve the potential quality of the cDNA sequence, a need exists for heuristics that consider the coding potential of the assembly consensus when choosing between alternative alignments.

SUMMARY OF THE INVENTION

Accordingly, one aspect of the present invention is a method of maximizing open reading frame length in an assembly consensus sequence comprising identifying frameshift ambiguities in the consensus sequence wherein the number of frameshift ambiguities is N; dividing the consensus sequence into N+1 fragments split by the identified frameshift ambiguities; generating a matrix of score values for each frameshift ambiguity in each frame from the fragment immediately following the frameshift ambiguity, where the matrix has N columns and three rows; applying a scoring metric that allocates a value to a translation product of a sequence from one or more fragments wherein the value reflects the likelihood that the sequence is a real coding sequence; repeating the steps above for the reversed complement of the consensus sequence; rebuilding the consensus sequence wherein the highest scoring reading frame in the highest scoring direction is optimized; and displaying the rebuilt consensus sequence on an output device.

Yet another aspect of the invention is computer systems and computer readable media for performing the methods of the invention.

DETAILED DESCRIPTION OF THE INVENTION

All publications from the scientific literature cited in this specification are herein incorporated by reference as though fully set forth.

The method of the invention presents robust computational methods (algorithms) that optimize the protein coding potential of a consenus where an assembly contains EST sequencing errors that lead to alternative consensus sequences. The algorithms employ a dynamic programming approach to allow base or gap insertion in ambiguous regions in EST assemblies to maximize open reading frame length in the consensus, improving the coding potential of the consensus sequence and the sequence comparison score between the optimized assembly and best homolog.

Algorithms of the invention present a measurable improvement in the quality of assembly consensus sequences and give a very good estimate of the correct translation product. Consequently, the algorithms provide an optimized assembly of ESTs providing for translation of accurate protein sequences which can be further analyzed.

Figure 1:
FIG. 1 diagrams a portion of an assembly and consensus sequence showing ambiguous sites.

FIG. 1 shows an assembly and its consensus with three types of ambiguous sites highlighted. In a majority situation, there is disagreement on a base call but one contender is present in more ESTs than other bases. In a tied majority situation, no one base is present in higher proportions than another. For each of these ambiguities, a consensus building algorithm is required to make a decision on which base to insert. In a gap ambiguity situation, gaps are present in equal or higher proportion to non-gaps. Base calls where there is no clear majority in the alignment of components may lead to the inclusion of an incorrect gap or extraneous base causing a frameshift error. As used herein, these sites are termed "frameshift ambiguities" and it is on these sites that the algorithm of the invention operates.

There are two types of frameshift ambiguity, those that have a gap in the consensus sequence and those that have a non-gap. If there is a gap in the consensus and the non-gap majority candidate is inserted, the reading frame shifts forward one position. As used herein, this is a "positive frameshift." Conversely, if there is a base in the consensus and a gap is inserted, the reading frame falls back one position resulting in a "negative frameshift."

Each frameshift ambiguity in a sequence allows two choices that will affect the reading frame, gap or non-gap. In a consensus sequence with N frameshift ambiguities there will be $2^N$ possible consensus sequences and $6 \times 2^N$ possible reading frames. For many assembly consensus sequences the prospect of evaluating all possible combinations, rapidly becomes computationally untenable for large numbers of frameshift ambiguities. The algorithm of the invention employs a dynamic programming technique which performs the evaluation in O(N) rather than O($2^N$) comparisons, allowing examination of all reading frames and selection of the one judged to have the most likely translation product.

In one embodiment, the invention provides a method of maximizing open reading frame length in an assembly consensus sequence comprising:

a. identifying frameshift ambiguities in a consensus sequence wherein the number of frameshift ambiguities is N;

b. dividing the consensus sequence into N+1 fragments split by the identified frameshift ambiguities;

c. generating a matrix of score values for each frameshift ambiguity in each frame from the fragment immediately following the frameshift ambiguity, where the matrix has N columns and three rows;

d. applying a scoring metric that allocates a value to a translation product of a sequence from one or more fragments wherein the value reflects the likelihood that the sequence is a real coding sequence;

e. repeating steps a through d for the reversed complement of the consensus sequence;

f. rebuilding the consensus sequence wherein the highest scoring reading frame in the highest scoring direction is optimized; and g. displaying the results of step (f) on an output device.

Preferably, the frameshift ambiguities are identified by determining the proportion of gaps within a defined range. Preferably, the defined range is about 0.5 to about 0.7.

The algorithm uses a scoring metric to evaluate the fractions in each of the three frames between the frameshift ambiguities. The scoring metric can be any scheme that allocates a value to the translation product of a sequence fragment, such that it reflects the likelihood that the fragment is a real coding sequence rather than a random (out of frame) translation. Exemplary schemes allow only the accumulation of scores between neighboring fragments provided there are no intervening stop codons. Particularly preferred is the longest ORF scoring metric, where the longest stretch of amino acids uninterrupted by a stop codon downstream from the frameshift ambiguity is determined. In the longest ORF scoring metric, scores are accumulated by adding the matrix score value of column X row Y to the highest of two matrix values in column X−1, row Y or column X−1, row Z wherein X=1 to N−1 and Y=1 to 3 and Z is the remainder of (Y+1)/3 for positive frameshifts or the remainder of (Y+2)/3 for negative frameshifts. In this metric, a separate record of those ambiguity resolutions where the score is added from column X−1, row Z may be kept for each frame. Other exemplary scoring metrics examine the fragment in isolation from other fragments for the number of stop codons or the frequency of rare codons. Still other schemes include hexamer frequency; searching for 5' and 3' untranslated regions (UTRs) for sequence features such as TATAA boxes and poly-A tails; nucleotide and oligonucleotide composition (Fickett, *Nucleic Acids Res.* 10, 5303–5318 (1982) and Solovyev, *Nucleic Acids Res.* 22, 5156–5163 (1994)); amino acid composition and low complexity (Saqi, *Protein Eng.* 8, 1069–1073 (1995)); physicochemical and steric properties (Ladunga and Smith, *Protein Eng.* 20, 101–110 (1997)); secondary structure; and complex ORF prediction algorithms as disclosed by Birney in *Nucleic Acids Res.* 24, 2730–2739 (1996).

In addition to display on an output device such as a monitor or a printer, the modified consensus sequences can be stored in a database. The methods of the invention can further comprise the step of characterizing the modified consensus sequence. Characterization can be done on the basis of of sequence, structure, biological function or other related characteristics. Once categorized, the database can be expanded with information linked to biological function, structure or other characteristics. Further, modified consensus sequences can be characterized on the basis of expert commentary from relevant human specialists or by the results of biological experiments. If desired, the modified consensus sequences generated by the method may be confirmed experimentally by techniques well known to those skilled in the art. The algorithm of the invention employs a series of method steps described below that are repeated for both the forward and reverse directions in the assembly consensus sequence. If two sequences agree on a base and are in opposite directions, then their weight in establishing majority is doubled.

Figure 2:
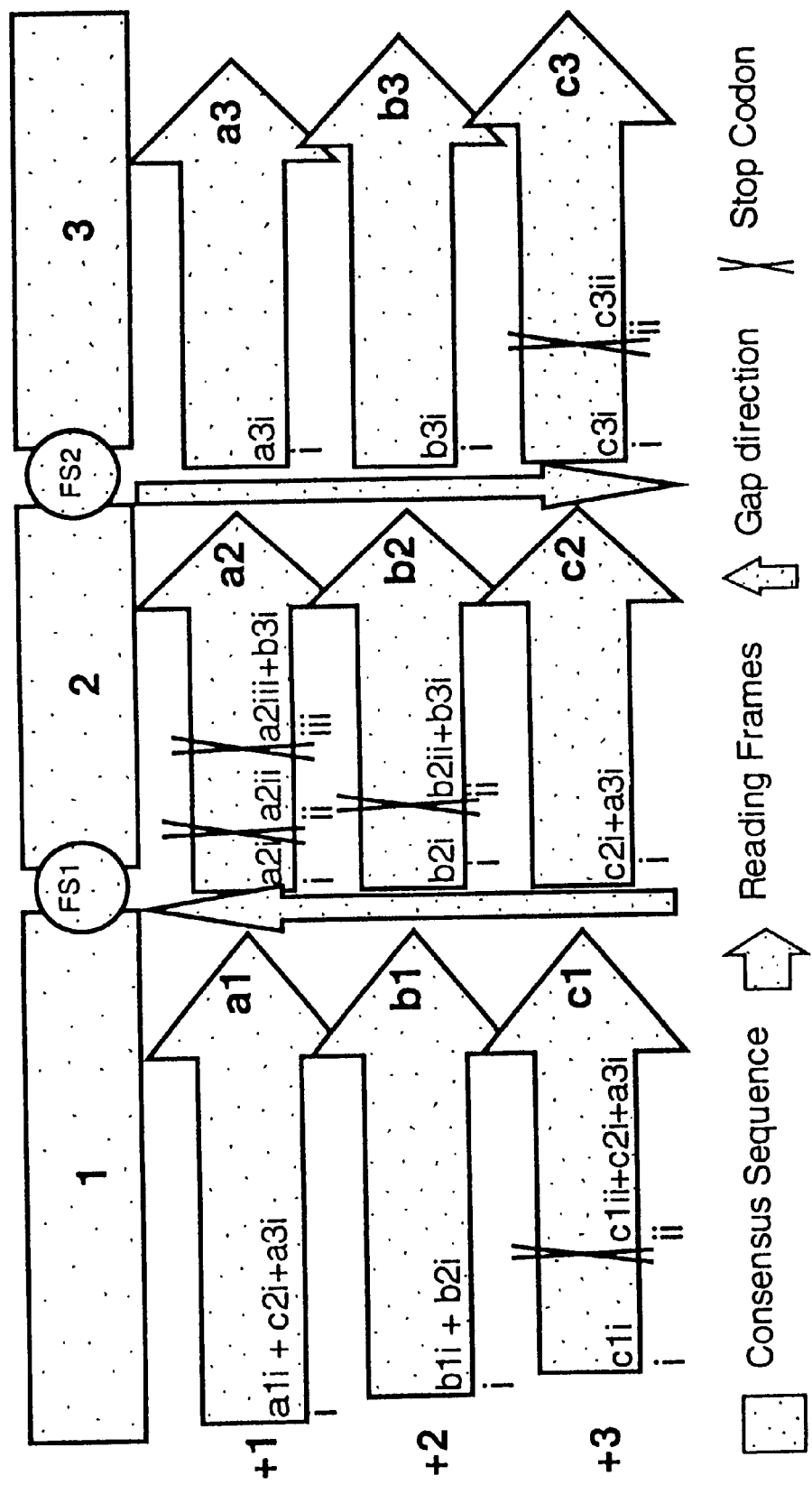
FIG. 2 shows a dynamic programming scoring schematic with final scores included.

1. The assembly is examined and the N frameshift ambiguities in the consensus are identified as sites where the proportion of gaps is between an upper and lower bound. By default, these parameters are set to the range 0.5 to 0.7. In FIG. 2, the two ambiguities are labeled FS1 and FS2.

2. The consensus is divided into N+1 fractions split by successive frameshift ambiguities. In FIG. 2, these fractions are labeled a1 to a3 for frame +1 through c1 to c3 for frame +3.

3. For each frameshift ambiguity, and in each frame, a score is generated filling a matrix of N cells. The score for a cell is generated from the sequence immediately following the ambiguity up to the next ambiguity or the end of the sequence. The metric for generating the score is based on the likelihood that the sequence fragment is a coding region. Preferably, the metric is the distance from the ambiguity to the first stop codon, referred to herein as "ORF length." In FIG. 2, the score matrix has two columns, one for FS1 and one for FS2. At this step, Score (FS1, frame +1) is a2 and Score (FS2, Frame +2) is b3.

4. Proceeding from column N−1 of the matrix leftwards to column 1, each cell has its score added to the highest scoring of two possible cells from the column to its right provided that there is no stop codon in the downstream fraction between.

For a cell in column c, row r, with score S(c, r), either no change to the consensus occurs, or there is a gap insertion or deletion depending on the type of frameshift ambiguity at that base:

For a positive frameshift:

$$S(c, r) \leftarrow \max \begin{pmatrix} S(c, r) + S(c + 1, (r + 1) \%3) \\ S(c, r) + S \end{pmatrix}$$

For a negative frameshift:

$$S(c, r) \leftarrow \max \begin{pmatrix} S(c, r) + S(c + 1, (r + 2) \%3) \\ S(c, r) + S(c + 1, r) \end{pmatrix}$$

Where x %3 (x mod 3) means the remainder after division of x by 3. Further, if there has been change to the consensus indicated by the addition of scores between non-adjacent cells, it is recorded.

In FIG. 2, Score(FS1, Frame +3) at this step wold be $c2_i+a3_i$ and for frame +3, an ambiguity change at FS1 is recorded.

5. For each cell, if there was a stop codon (or for column 1, the sequence start) in that frame in the fraction immediately upstream, add the score for that fraction to the cell score. Score (FS1, Frame +3) would now be changed to $c1_{ii}+c2_i+a3_i$ as shown in FIG. 2.
6. The maximum score in all matrix cells is found, determining which frame has the optimum sequence. In FIG. 2 this would be Score (FS1, Frame +1) which is $a1_i+c2_i+a3_i$.

It is possible that a higher scoring sub-sequence occurs between two stop codons in a single fraction. Accordingly, any such sub-sequence is checked and compared to the maximum score. In FIG. 2, the sub-sequence identified with the score $a2_{ii}$ is exemplary.

7. The consensus sequence is rebuilt for the frame with the maximum score using the frame-specific list of ambiguity resolutions to dictate the same changes that described a path through the matrix. For example in FIG. 2, the best sequence would be in Frame +1 requiring a gap deletion at FS1 and a gap insertion at FS2.
8. The algorithm is repeated for the reversed assembly. Stop codons are recalculated for each frame of the reversed complement of the consensus, and in an assembly with B bases, each frameshift ambiguity at position $P_i$ is moved to position $B-P_i+1$.
9. The new consensus sequence is presented with the gaps inserted to optimise the highest scoring reading frame in the highest scoring direction.

Figure 3:
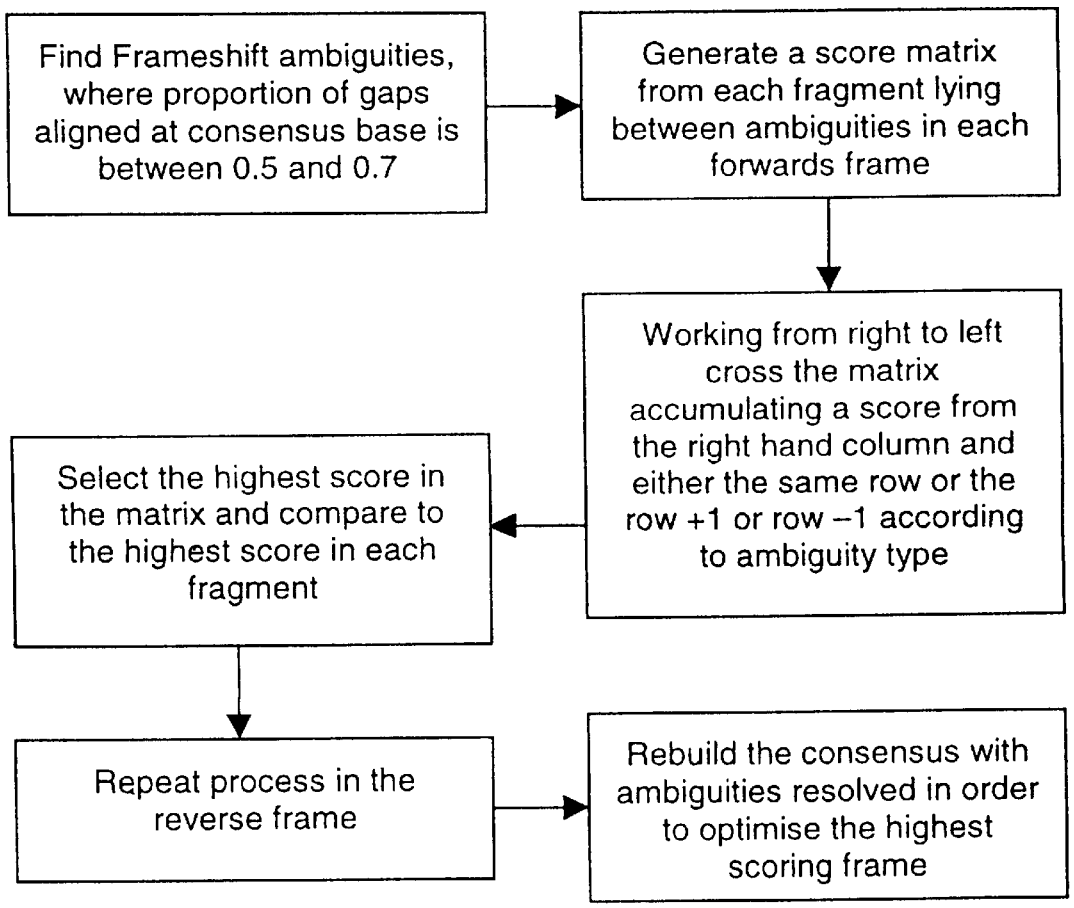
FIG. 3 shows an algorithm of the invention in flowchart form.

FIG. 2 shows the dynamic programming schematic with final scores included. The consensus sequence has two frameshift ambiguities. At FS1 in the unmodified sequence there is a non-gap and at FS2 there is a gap. If the algorithm inserts a gap at FS1, then from that point onward the frame will shift back one, from +2 to +1, from +1 to +3 or from +3 to +2. The algorithm works from right to left and in each fraction of the reading frame between ambiguities, it accumulates a score from either the fraction to the right in the same frame or the shifted frame according to the type of ambiguity. A flowchart presentation of the algorithm is shown in FIG. 3.

Another aspect of the invention is a computer system for maximizing ORF length in an assembly consensus sequence. A representative computer system includes a hardware environment on which the methods of the invention may be implemented. The hardware environment includes a central processing unit, a memory device, a display and a user interface device. An exemplary hardware environment is a Sun Microsystems Ultra 1 running a UNIX operating system, having a display and keyboard and/or mouse input devices.

In another embodiment, the computer system for maximizing ORF length in an assembly consensus sequence comprises:

a. means for identifying frameshift ambiguities in the consensus sequence wherein the number of frameshift ambiguities is N;
b. means for dividing the consensus sequence into N+1 fragments split by the identified frameshift ambiguities;
c. means for generating a matrix of score values for each frameshift ambiguity in each frame from the fragment immediately following the frameshift ambiguity, where the matrix has N columns and three rows;
d. means for applying a scoring metric that allocates a value to a translation product of a sequence from one or more fragments wherein the value reflects the likelihood that the sequence is a real coding sequence;
e. means for repeating steps a through d for the reversed complement of the consensus sequence;
f. means for rebuilding the consensus sequence wherein the highest scoring reading frame in the highest scoring direction is optimized; and
g. means for displaying the results of step (f) on an output device.

In another embodiment, the computer system comprises a central processing unit executing a ORF length maximizing program stored in a memory device accessed by the central processing unit; a display on which the central processing unit displays screens of the program in response to user inputs; and a user interface device.

Another aspect of the invention is a computer readable medium containing program instructions for maximizing open reading frame length in an assembly consensus sequence, the program instructions comprising:

a. identifying frameshift ambiguities in the consensus sequence wherein the number of frameshift ambiguities is N;
b. dividing the consensus sequence into N+1 fragments split by the identified frameshift ambiguities;
c. generating a matrix of score values for each frameshift ambiguity in each frame from the fragment immediately following the frameshift ambiguity, where the matrix has N columns and three rows;
d. applying a scoring metric that allocates a value to a translation product of a sequence from one or more fragments wherein the value reflects the likelihood that the sequence is a real coding sequence;
e. repeating steps a through d for the reversed complement of the consensus sequence;
f. rebuilding the consensus sequence wherein the highest scoring reading frame in the highest scoring direction is optimized; and
g. displaying the results of step (f) on an output device.

The present invention will now be described with reference to the following specific, non-limiting examples.

EXAMPLE 1

Reconstruction of Assembly Sequences

An algorithm of the invention was written in ANSI C and compiled using the Digital OSFI compiler under Digital Unix Version 4.0. All testing was completed on a Digital Personal Workstation 500au.

For analysis of algorithm performance, assemblies of public domain ESTs were selected at random from a subset of assemblies that had at least one frameshift ambiguity and at least two EST components. Of the candidates, 97.3% had frameshift ambiguities (the remainder had insufficient disagreement between their EST components to generate ambiguity) and could be modified by the algorithm of the invention. The remaining assemblies were excluded from the test set. Two DNA sequence sets, in which set 2 was modified by the algorithm using a longest ORF scoring metric, were compiled from the assemblies.

In order to evaluate the improvement in the assembly consensus sequences, homology searches were performed on the consensus sequence against the SwissProt protein database, release 35 (Bairoch and Apweiler, *Nucleic Acids Res.* 26, 38–42 (1998)) in all six reading frames. Nucleotide consensus sequences were evaluated by the blastx2 algorithm version 2.0a8 of Gish and States (*Nature Genet.* 3, 266–272 (1993)). Three measures of performance, namely score and alignment length of the best high scoring pair (HSP) and number of HSPs in the best alignment, were taken from the blastx results. The blastx score is a product of the length of the alignment, the gap penalty and the score matrix used in the blast algorithm. The score generated by the blast algorithm is strongly correlated to the length of the alignment and the gap penalty used. A significant increase would be expected if there has been an improvement to the consensus sequence. HSPs are the number of high scoring pairs aligned between the consensus and its putative translation product. If the reading frame is shifted then there will be one HSP aligning before the frameshift and one after. Blast programs report HSPs where two alignments cannot be joined because they are either separated by a break in homology or they are in different frames because of a frameshift error. Consequently, a reduction in the number of HSPs is expected as frameshift errors are corrected and HSPs combine into alignments comprising two or more unified HSPS. The results in Table 1 illustrate the improvements in the modified consensus registered by the blastx2 algorithm, all of which were measured and shown to be highly significant improvements (P-value<0.001 in a one-tailed t-test).

TABLE 1

Blastx2 search results

|  | Raw Consensus | Modified |
| --- | --- | --- |
| Score | 311.96 | 324.08 |
| HSPs | 1.54 | 1.45 |
| Length | 311.96 | 324.08 |

The frame in which the modified consensus aligned in the blastx2 algorithm with a Poisson probability of less than $10^{-100}$ was examined further. These alignments give a reliable indication of how well the algorithm of the invention is predicting the correct reading frame. The results indicated that the longest ORF in the unmodified consensus fell into the correct reading frame 36% of the time while in the modified consensus the predicted ORF aligned to the correct reading frame in 80% of the alignments.

EXAMPLE 2

Translation Product Prediction Results

The algorithm of the invention also delivers a reading frame prediction from an assembly from which a predicted protein product is generated. Taking the predicted reading frame in the new consensus generated by the maximum ORF length scoring metric, the test sequences were translated to generate putative translation products. The resulting protein sequences were trimmed to give the longest stretch between stop codons. The blastp algorithm version 2.0a8 of Altschul et al. (*J. Mol. Biol.* 215, 403–410 (1990)) was used to compare the predicted protein product to the SwissProt database, supra.

For comparison, the raw consensus sequence was translated to give its longest contiguous translation product (longest region between stop codons). This sequence was also searched against the same database. For both sets of proteins, 900 of the 903 test sequences formed an alignment to a protein sequence from SwissProt. Mean values from the blastp2 algorithm are presented in Table 2 and show a highly significant increase in score, length and identity. The most striking improvements are in the alignment length and the alignment score, both of which are closely linked. Also, a significant decrease in Poisson probability was observed.

TABLE 2

Blastp search results

|  | Raw Consensus | Modified |
| --- | --- | --- |
| Score | 141.40 | 243.31 |
| Probability | 0.222 | 0.195 |
| Length | 61.56 | 87.43 |
| % Identity | 47.04 | 52.48 |

The sequence score is expected to improve as the alignment covers a longer stretch of the sequence. The results reflect a 72.07% improvement over the raw consensus. Since the score is linearly proportional to the sequence length for a given alignment and the improvement in length reflects a 42.02% increase this implies that the overall quality of the alignments has also risen, which implication is supported by the observed improvement in sequence identity.

It will be apparent to those skilled in the art that various modifications can be made to the present method without departing from the scope or spirit of the invention, and it is intended that the present invention cover modifications and variations of the method provided they come within the scope of the appended claims and their equivalents.

I claim:

1. A method of maximizing open reading frame length in an assembly consensus sequence comprising:
   a. identifying frameshift ambiguities in the consensus sequence wherein the number of frameshift ambiguities is N;
   b. dividing the consensus sequence into N+1 fragments split by the identified frameshift ambiguities;
   c. generating a matrix of score values for each frameshift ambiguity in each frame from the fragment immediately following the frameshift ambiguity, where the matrix has N columns and three rows;
   d. applying a scoring metric that allocates a value to a translation product of a sequence from one or more fragments wherein the value reflects the likelihood that the sequence is a real coding sequence;
   e. repeating steps a through d for the reversed complement of the consensus sequence;
   f. rebuilding the consensus sequence wherein the highest scoring reading frame in the highest scoring direction is optimized; and
   g. displaying the results of step (f) on an output device.

2. The method of claim 1 wherein the frameshift ambiguities are identified by determining the proportion of gaps within a defined range.

3. The method of claim 2 wherein the defined range of the proportion of gaps is about 0.5 to about 0.7.

4. The method of claim 1 wherein the scoring metric accumulates scores between neighboring fragments provided there are no intervening stop codons.

5. The method of claim 4 wherein the scores are accumulated by adding the matrix score value of column X row Y to the highest of two matrix values in column X−1, row Y or column X−1, row Z wherein X=1 to N−1 and Y=1 to 3 and Z is the remainder of (Y+1)/3 for positive frameshifts or the remainder of (Y+2)/3 for negative frameshifts.

6. A computer system for maximizing open reading frame length in an assembly consensus sequence comprising:

a. means for identifying frameshift ambiguities in the consensus sequence wherein the number of frameshift ambiguities is N;

b. means for dividing the consensus sequence into N+1 fragments split by the identified frameshift ambiguities;

c. means for generating a matrix of score values for each frameshift ambiguity in each frame from the fragment immediately following the frameshift ambiguity, where the matrix has N columns and three rows;

d. means for applying a scoring metric that allocates a value to a translation product of a sequence from one or more fragments wherein the value reflects the likelihood that the sequence is a real coding sequence;

e. means for repeating steps a through d for the reversed complement of the consensus sequence;

f. means for rebuilding the consensus sequence wherein the highest scoring reading frame in the highest scoring direction is optimized; and g. means for displaying the results of step (f) on an output device.

7. A computer readable medium containing program instructions for maximizing open reading frame length in an assembly consensus sequence, the program instructions comprising:

a. identifying frameshift ambiguities in the consensus sequence wherein the number of frameshift ambiguities is N;

b. dividing the consensus sequence into N+1 fragments split by the identified frameshift ambiguities;

c. generating a matrix of score values for each frameshift ambiguity in each frame from the fragment immediately following the frameshift ambiguity, where the matrix has N columns and three rows;

d. applying a scoring metric that allocates a value to a translation product of a sequence from one or more fragments wherein the value reflects the likelihood that the sequence is a real coding sequence;

e. repeating steps a through d for the reversed complement of the consensus sequence;

f. rebuilding the consensus sequence wherein the highest scoring reading frame in the highest scoring direction is optimized; and g. displaying the results of step (f) on an output device.

* * * * *

UNITED STATES PATENT AND TRADEMARK OFFICE
CERTIFICATE OF CORRECTION

PATENT NO. : 6,047,109
DATED : April 4, 2000
INVENTOR(S) : Alex J. Whittaker

It is certified that error appears in the above-identified patent and that said Letters Patent is hereby corrected as shown below:

<u>Title Page</u>:
Under "Publications" after "Attorney, Agent, or Firm", please delete "Keith Rutter".
Under "Publications" after "Attorney, Agent, or Firm", please add "Kirk Baumeister".

Signed and Sealed this

Third Day of July, 2001

Attest:

NICHOLAS P. GODICI
*Attesting Officer*     *Acting Director of the United States Patent and Trademark Office*